United States Patent [19]

Deibig et al.

[11] Patent Number: 4,990,146
[45] Date of Patent: Feb. 5, 1991

[54] CONTAINERS OF AMINOPOLYMERS

[75] Inventors: Heinrich Deibig, Guensberg; Albrecht Dinkelaker, Biberist, both of Switzerland

[73] Assignee: Belland AG, Solothurn, Switzerland

[21] Appl. No.: 283,193

[22] Filed: Dec. 12, 1988

[30] Foreign Application Priority Data

Dec. 15, 1987 [DE] Fed. Rep. of Germany ....... 3742472

[51] Int. Cl.$^5$ .......................... A61F 5/44; A61F 25/00
[52] U.S. Cl. ...................................... 604/332; 526/332
[58] Field of Search .......................... 526/312; 604/332; 128/DIG. 24

[56] References Cited

U.S. PATENT DOCUMENTS

| | | | |
|---|---|---|---|
| 4,358,567 | 11/1982 | Hayama et al. | 525/359.4 |
| 4,362,158 | 12/1982 | Lena | 128/DIG. 24 |
| 4,596,573 | 6/1986 | Donnan et al. | 128/DIG. 24 |
| 4,762,738 | 8/1988 | Keyes et al. | 604/332 |

FOREIGN PATENT DOCUMENTS

| | | |
|---|---|---|
| 0010171 | 9/1979 | European Pat. Off. . |
| 0032244 | 12/1980 | European Pat. Off. . |
| 0143935 | 9/1984 | European Pat. Off. . |
| 2726461 | 12/1977 | Fed. Rep. of Germany . |
| 2800520 | 7/1978 | Fed. Rep. of Germany . |
| 2312817 | 12/1978 | Fed. Rep. of Germany . |
| 2934086 | 4/1981 | Fed. Rep. of Germany . |
| 3335954 | 4/1985 | Fed. Rep. of Germany . |
| 8106631 | 10/1981 | France . |
| 2043077 | 10/1980 | United Kingdom . |
| 2083762 | 3/1982 | United Kingdom ................ 604/332 |

OTHER PUBLICATIONS

Hochmolekularberichi 1986, Lion Corp. V1-27.

Primary Examiner—Joseph L. Schofer
Assistant Examiner—Alex H. Walker
Attorney, Agent, or Firm—Lackenbach Siegel Marzullo & Aronson

[57] ABSTRACT

The invention relates to amino group-containing polymers, which are produced by the polymerization of acrylates with aminoacrylates in the forms of esters of acrylic or methacrylic acid with amino alcohols. Polymers of this type are insoluble in the neutral to basic aqueous medium, but are soluble in the acid medium. They are particularly suitable for the production of colostomy bags.

12 Claims, No Drawings

CONTAINERS OF AMINOPOLYMERS

BACKGROUND OF THE INVENTION

European Pat. No. 32 244 describes a composite film or sheet, in which one layer is made from a material which is insoluble in water, but soluble in acid or basic aqueous media. The material is preferably a copolymer of an unsaturated organic carboxylic acid with a neutral monomer.

EP-OS 143 935 describes copolymers of acrylate and acrylic ormethacrylic acid insoluble in water, but soluble in a basic medium which can be used in may different ways and which have good mechanical characteristics.

The object of the present invention is to make available polymers, which are insoluble in a neutral and basic medium, but can be dissolved in acid, aqueous media.

The invention therefore relates to amino group-containing polymers of at least one acrylate of formula I

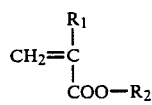     I in which $R_1$ is hydrogen or methyl and $R_2$ an alkyl radical with 1 to 18 C-atoms, and an amino acrylate of formula II

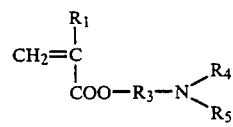     II in which $R_1$ has the same meaning as hereinbefore and $R_3$ is an alkyl radical with 1 to 6 C-atoms and $R_4$ and $R_5$ are the same or different and represent hydrogen or alkyl radicals with 1 to 4 C-atoms, as sell as optionally neutral vinyl monomers, which differ from the acrylates of formula I, and conventional polymer additives.

Polymers with the above composition represent a valuable supplement to the known polymers soluble in basic media and make available numerous new possible uses.

The radical $R_2$ of the monomers of formula I is preferably an alkyl radical with 1 to 4 C-atoms. Typical representatives of monomers of formula I are methyl methacrylate, ethyl acrylate, butyl acrylate and butyl methacrylate. In the aminoacrylates of formula II, the radical $R_3$ is preferably C2. The radicals $R_4$ and $R_5$ are preferably alkyl radicals, especially methyl or ethyl. A nitrogen atom can also be located within a ring provided in place of the radicals $R_4$ and $R_5$, e.g. in a morpholine ring. A particularly suitable representative of the amino acrylates is dimethylaminoethyl methacrylate.

The third monomer can be a monomer of the group of vinyl ethers with 3 to 18 C-atoms, particularly vinyl isobutyl ethers, aromatic vinyl hydrocarbons with 8 to 11 C-atoms, particularly styrene, acrylate or methacrylate with an alcohol radical with 1 to 18 C-atoms, particularly n-butyl acrylate, butyl methacrylate and stearyl methacrylate.

The molar ratio of the monomers of formula I to the monomers of formula II is preferably in the range 8:1 to 2:1, particularly 6:1 to 3:1. The ratio of the aminoacrylate to the terpolymer, provided that one is present, is preferably 1:0.1 to 1:1, particularly 1:0.2 to 1:0.3. The molecular weight of the polymers is preferably in the range 40,000 to 200,000 particularly 50,000 to 80,000.

For the production of the inventive polymers, the monomers are preferably polymerized directly in the form of the acrylate or aminoacrylate.

Polymerization can take place continuously and for this purpose use is made of special extruders, particularly installations with several series-connected extruders. The polymers can be in different states, e.g. in the form of solutions or dispersions, which are usable for adhesive joints or coatings, as well as powders. As a result of their thermoplastic characteristics, they can also be present in the form of shaped articles, particularly granules, films, deep drawn parts, injection moulded parts, pressed or blown parts and plates. These shaped articles can be provided with acid sensitive coatings, in order to make them water-soluble on the side provided with the coatings.

The polymers according to the invention are particularly suitable for use in the production of dissolvable containers, which are intended to receive feces, particularly for the production of colostomy bags.

Colostomy bags are used for collecting feces in the case of artificial intestinal outlets. Their elimination after use represents a problem, because the sheets or films used are extremely mechanically and chemically stable. As feces have a neutral to basic pH-value, for the internal coating of such collecting containers it is particularly appropriate to use plastics, which are insoluble in the neutral to basic range, but can be dissolved in the acid range. As stated above, this is the case with the inventive polymers.

The colostomy bag or other containers can be made from a sheet of a plastic stable in the basic and neutral range and can then be made soluble with acid material after use by immersion or contact in some other way. Preference is however given to systems into which the acid is already incorporated, so that they are also soluble in the neutral aqueous medium and an acid does not have to be kept separately ready. For this purpose a sheet or film can be constructed as a composite sheet or film with at least two layers, in which a layer adjacent to the outside is acid-soluble, but neutral or basic medium-stable inner layer can comprise acid material or can contain such a material. The acid layer is preferably water-soluble, so that it releases the acid on dissolving and said acid then acts as a dissolving agent for the inner coating soluble in the acid medium. The composite sheet can additionally contain a vapour or odour barrier and an aluminum foil or coating is suitable for this. The aluminum coating can be so thin that it decomposes during the dissolving of the sheets. However, the aluminum coating can also be incorporated between film coatings, e.g. between said acid coating and an outer water-soluble coating, in which the substances can be incorporated which bring about a destruction of the aluminum foil at the time of water access, such as alkalis or oxidizing substances. Finally the container or bag can be provided on its outside with at least one skin-compatible protective layer, which can have on its outside a textile flock covering or the like. This prevents any unpleasant perspiration for the bag wearer and also an undesired pre-dissolving due to perspiration.

Other features and advantages of the invention can be gathered from the following examples in conjunction with the subclaims. The individual features can be realized alone or in combination with one another.

EXAMPLE 1

In a double-walled stirred vessel cooled to 20° C. are dissolved 60 mole (51.6 kg) of methyl acrylate, 10 mole (15.7 kg) of dimethylaminoethylmethacrylate (hereinafter called DIMA) and 0.5 kg of axobisdiisobutyronitrile (hereinafter called AIBN) and this reaction mixture is pumped at a rate of 10 kg/h into the filling zone of a diameter 60 mm, length 2580 mm closely meshing twin-screw extruder rotating in the same direction. The extruder, hereinafter referred to as a reactor, has ten temperature controllable (heatable and coolable) zones. The pumpingin zone has a temperature of 80° C., zones 2 to 10 being at 105° C. In the case of a reactor speed of 30 rpm a current consumption of 9 Åis measured and the pressure at the end of the reactor was 8 bar.

The polymerization mixture was conveyed from the reactor by means of flow lien into a second extruder having diameter 30 mm, length 1300 mm closely meshing twin-screws extruder rotating in the same direction. This is referred to as a compounder hereinafter.

The compounder has six heatable and coolable zones. Zone 2 (considered from the reactor) carries a fractionating column, zones 3 and 4 being connected with vacuum pumps for removing residual monomers and solvents. The compounder temperatures are 140° C. in zone 1, 180° C. in zones 2, 3 and 4 and 120° C. in zone 6 (extruder head, dies).

0.6 kg/h of unpolymerized monomers are distilled off from the reactor polymerization mixture and the power consumption in the compounder is 20 Å. The polymer leaves the compounder in the form of strands, which are cooled on cooling rollers and are granulated in a granulator.

The granules have an analytically determined (Kjeldahl) nitrogen content ob 2.6% (theoretically 2.1%). From the granules it is possible to produce transparent films or sheets, which are stable with respect to neutral and basic water, but dissolve in dilute acids. The water-insolubility and acid-solubility make the products very suitable for temporary protective and covering functions, as well as a intermediate aids in processing processes.

EXAMPLE 2

On using, in place of the formulations of Example 1, 50 mole (50 kg) of ethylacrylate, 10 mole (15.7 kg) of DIMA and 0.5 kg of AIBN, then a copolymer with 2.5% N (theoretically 2.1 N) and similar characteristics is obtained.

EXAMPLE 3

If in place of the formulations of Example 1, 40 mole (56.8 kg) of butylmethacrylate, 10 mole (15.7 kg) of DIMA and 0.5 kg of AIBN are used, then a copolymer with 2.4 % N (theoretically 1.9% N) and similar characteristics is obtained.

We claim:

1. A flexible container, having a composite, layered, synthetic, copolymeric construction having aminogroups, said copolymer comprising:
   (a) a first monomer having the formula

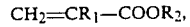

wherein $R_1$ is hydrogen or methyl and $R_2$ is an alkyl radical with from 1 to 18 carbon atoms,
   (b) a second amino monomer having the formula

wherein $R_1$ is the same as before, $R_3$ is an alkyl radical having 1 to 6 carbon atoms and R4 and R5 are the same or different and represent hydrogen or alkyl radicals having 1 to 4 carbon atoms,
   (c) the molar ratio of the first monomer to the second monomer is from 8 to 1 to 2 to 1, and
   (d) a third monomer selected from the group consisting of a vinyl ether having 3 to 18 carbon atoms, aromatic vinyl hydrocarbons having 8 to 11 carbon atoms, and acrylates or methacrylates of alcohols having 1 to 18 carbon atoms, and mixtures thereof, and present to the extent of from zero to 16 molar percent,
   wherein the molecular weight of the copolymer is from 40,000 to 200,000 daltons.

2. A copolymeric container as in claim 1, wherein the molar ratio of the first monomer to the second monomer is from 6 to 3.

3. A copolymeric container as in claim 1, wherein the molar ratio of the second monomer to the third monomer is from 10 to 2.5.

4. A copolymeric container as in claim 1, wherein the inner layer adjacent to the contents is stable to basic, aqueous media and soluble in dilute acid and the outer layer adjacent to the atmosphere is soluble in water.

5. A copolymeric container as in claim 1, wherein the water-soluble outer layer comprises acid groups.

6. A copolymeric container as in claim 1, further comprising a vapor-proof barrier.

7. A copolymeric container as in claim 6, wherein the vapor-proof barrier is aluminum foil.

8. A copolymeric container as in claim 1, wherein the aromatic vinyl hydrocarbon having 8 to 11 carbon atoms is styrene.

9. A copolymeric container as in claim 1, wherein the first monomer is methyl acrylate and the second monomer is dimethylaminoethyl methacrylate.

10. A copolymeric container as in claim 1, wherein the first monomer is ethyl acrylate and the second monomer is dimethylaminoethyl methacrylate.

11. A copolymeric container as in claim 1, wherein the first monomer is butyl acrylate and the second monomer is dimethylaminoethyl methacrylate.

12. A copolymeric container as in claim 4, wherein the outer layer comprises textile flock.

* * * * *